(12) United States Patent
Biglieri et al.

(10) Patent No.: US 7,348,774 B2
(45) Date of Patent: Mar. 25, 2008

(54) METHOD AND AN APPARATUS FOR IMAGE ACQUISITION AND DISPLAY BY MEANS OF NUCLEAR MAGNETIC RESONANCE IMAGING

(75) Inventors: Eugenio Biglieri, Masio (IT); Luigi Satragno, Genoa (IT)

(73) Assignee: Esaote, S.p.A., Casale Monferrato (IT)

( * ) Notice: Subject to any disclaimer, the term of this patent is extended or adjusted under 35 U.S.C. 154(b) by 545 days.

(21) Appl. No.: 10/852,119

(22) Filed: May 25, 2004

(65) Prior Publication Data

US 2005/0267352 A1 Dec. 1, 2005

(51) Int. Cl.
*G01V 3/00* (2006.01)
(52) U.S. Cl. ...................................... 324/307
(58) Field of Classification Search ......... 324/300–322
See application file for complete search history.

(56) References Cited

U.S. PATENT DOCUMENTS

| | | | |
|---|---|---|---|
| 4,734,646 A | | 3/1988 | Shenoy et al. |
| 4,871,966 A | * | 10/1989 | Smith et al. ................. 324/309 |
| 5,222,499 A | * | 6/1993 | Allen et al. .................. 600/426 |
| 5,245,282 A | * | 9/1993 | Mugler et al. ............... 324/309 |
| 5,438,263 A | * | 8/1995 | Dworkin et al. ............ 324/309 |
| 5,719,498 A | * | 2/1998 | Hausmann ................... 324/309 |
| 6,043,654 A | * | 3/2000 | Liu et al. ..................... 324/309 |
| 6,586,934 B2 | * | 7/2003 | Biglieri et al. .............. 324/309 |
| 6,668,083 B1 | * | 12/2003 | Verdonck et al. ........... 382/203 |
| 7,190,992 B2 | * | 3/2007 | Tatebayashi et al. ........ 600/410 |

OTHER PUBLICATIONS

M.A. Foster and J.M.S. Hutchison, "Practical NMR Imaging", IRL Press, pp. 22-24.
E. Mark Haacke, Ph.D., Robert W. Brown, Ph.D., Michael R. Thompson, Ph.D., and Ramesh Venkatesan, D.Sc., "Magnetic Resonance Imaging Physical Principles and Sequence Design", Wiley-Liss, pp. 194-195.

* cited by examiner

*Primary Examiner*—Brij Shrivastav
*Assistant Examiner*—Dixomara Vargas
(74) *Attorney, Agent, or Firm*—Buchanan Ingersoll & Rooney PC

(57) ABSTRACT

A method for image acquisition and display by Nuclear Magnetic Resonance Imaging, allowing display of images of an anatomical region along section planes or slices having different positions with respect to another, which method includes carrying out at least one three dimensional Magnetic Resonance Imaging for acquiring three dimensional anatomical data in the form of a three dimensional voxel array of unitary volumetric image elements in a user defined image volume containing at least part of the anatomical region to be studied and having a predetermined orientation reference; selecting relative to the user defined image volume one or more section planes along which an image of the anatomical region or part thereof in the defined volume is to be displayed; reconstructing from the three dimensional voxel array the image along each of the one or more section planes; displaying the image or images as a two dimensional image.

5 Claims, 6 Drawing Sheets

METHOD AND AN APPARATUS FOR IMAGE ACQUISITION AND DISPLAY BY MEANS OF NUCLEAR MAGNETIC RESONANCE IMAGING

BACKGROUND OF THE INVENTION

1. Technical Field

The invention relates to a method and to an apparatus for image acquisition and display by means of Nuclear Magnetic Resonance imaging (MRI) allowing the display of images of an anatomical region along section planes or slices having different positions and orientations one with respect to the other.

2. Discussion of Related Art

In the following description and in the claims, the terms "section plane" and "slice" have to be considered as having equivalent meanings. A section plane is a simplified representation of the reality, while slice is a term which better describes reality. Indeed strictly seen, a plane has no thickness while a slice a certain thickness. Nevertheless ideal conditions are considered when the slice thickness tends to be very small, so that the term section plane can be understood as the plane on which the ideal image is desired.

U.S. Pat. No. 4,871,966 discloses a technique known as Multi Slice Multi Angle. According to this method a two dimensional multislice image acquisition is carried out in which single two dimensional images are acquired along different slices or section planes, which section plane or planes may not be parallel or are not parallel one with respect to the other, but the planes have different orientations in space. The method disclosed in the said document allow the generation of images of slices of the anatomic region under examination which have different positions and orientations. The two dimensional images have different positions and orientations relative to only one axis of angular displacement of the said slices or section planes. Taking different images along selected slices having different positions and orientations is advantageous since it is possible to choose the slice orientation in such a way to match different diagnostic aims in order to obtain images of an anatomical region which better bring to evidence a pathological condition if present.

Nevertheless the limitation to the different positions and orientations only relative to only one axis of angular displacement strongly limits the capability of entirely imaging a region. An anatomical object such as for example an intervertebral disk may be oriented along a plane or may define a plane which has a different orientation with respect to the other disks relatively to two different axis of angular displacement. In this case a selected slice which orientation is defined relative to one of the axis of angular displacement could in certain circumstances cut only partially the disk or cut the disk at different depth, not coinciding with a central section plane of the corresponding disk.

If for example one considers to acquire images of axial slices which are positioned at the intervertebral disks in order to maximize the visualization capability of eventually occurring disk protrusions, the known technique would lead to an image of the protrusion only if it will fall on the selected section plane. If however the disk orientation is such that the plane defined by the disk is rotated in space relative to two axes of angular displacement, the protrusion may lay outside the selected image slice or section plane if this slice or section plane is oriented correspondingly to the orientation of the plane defined by the disk only relative to one of the two axis of angular displacement.

According to the known technique, the image slices are chosen having an orientation which is generally substantially parallel or coinciding with the position and orientation of the plane defined by the disk only relative to one axis of angular displacement. In case the spine is not rectilinear in shape according to two different transverse axes relative to the longitudinal extension of the spine, each slice which has to cross a disk must have a corresponding orientation in space relative to the said two axes so each slice must have different angles of orientation with respect to the image slices of other disks relative to the said two different transversal axis and this is equivalent to an angular displacement of the section plane or of the slice according to two different axis of rotation or angular displacement.

The capability of providing image slices of an anatomical region with a different orientation in space relatively to two or three axis of angular displacement or rotation becomes more important if considering anatomical districts having an even more complex structure than the spine.

A further draw back of the known method lies in the fact that a so called scout acquisition is needed in order to define the reference system for selecting the section plane or section planes along which the sequence of the two dimensional images has to be carried out. After having carried out this scout acquisition and having selected the slices an image acquisition sequence is started. Each image along each one of the selected slices is acquired separately and one after the other. If the patient displaces itself between the acquisition steps of the images along two successive image slices, than there is a risk that due to the displacement of the patient the slice along which the image is taken in the second acquisition step does not coincide with the slice image selected in the scout image. Thus the imaging session has to be repeated at least partially for example by repeating at least the scout image acquisition, the selection of the desired image slices and the sequence of the image acquisition steps along the selected image slices. This can be very time consuming if the user of the apparatus realizes that the patient has displaced itself. If however the user does not realize that the patient has changed its position the sequence of images acquired along the selected image slices does not correspond to the desired one and this could results in errors in reading the images and identifying a pathologic condition.

OBJECTS AND SUMMARY

Due to the fact that MRI allows the acquisition of images with well known three dimensional imaging sequences, the present invention suggests a method and an apparatus for image acquisition and display by means of Nuclear Magnetic Resonance imaging allowing the display of images of an anatomical region along section planes or slices having different positions and orientations one with respect to the other relative to only one, two or three axis of angular displacement or rotation, which method can be carried out at least with a comparable duration of the scanning procedure according to the known art, while allowing at the same time to improve resolution and to reduce problems relating to displacements of the object under examination during the scanning.

According to an embodiment of the present invention, the above mentioned aims are achieved by means of a method for image acquisition and display by means of Nuclear Magnetic Resonance Imaging, allowing the display of images of an anatomical region along section planes or slices having different position and orientations one with respect to the other, which method comprises the following steps:

a) carrying out at least one three dimensional Magnetic Resonance Imaging (3D MRI) for acquiring three dimensional anatomical data in the form of a three dimensional array of unitary volumetric image elements, so called voxels, in a user defined image volume containing at least part of the anatomical region to be studied and having a predetermined orientation reference in space;

b) selecting relative to the user defined image volume at least one, preferably a set of section planes, along which the image of the anatomical region of interest or part thereof being comprised in the defined volume has to be displayed;

c) reconstructing from the said three dimensional voxel array the images along the said section plane or planes;

d) displaying the said images as a two dimensional image.

It is important to notice that a three dimensional MRI scanning is carried out and that the signals received are processed in order to generate volumetric image data within a volume defined by the user. This volumetric image data, typically a three dimensional array of unitary image data volumes called voxels, can be achieved by means of several techniques. A multislice technique can be applied which is not very convenient since this technique is time consuming and will not fully allow satisfying in achieving the complete advantages of the present invention.

In a preferred embodiment, a 3D MRI technique is used to apply a 3D image acquisition sequence. This imaging technique allows to achieve a higher resolution as compared to two dimensional images. Typically, the thickness of the slice can be reduced at less than 1 mm. This is far less than the slice thickness that can be obtained using two dimensional imaging techniques. Gradients are better controlled and also a higher signal to noise relative ratio is typically obtained when providing for a voxel dimension and a duration of the scanning comparable with the two dimensional one.

By acquiring a three dimensional image a displacement of the patient during the acquisition has far less influence than for the known technique. As in the case of the known technique, displacements of the patient during acquisition will lead to artefacts, but since the image data of an entire volume is acquired the patient displacement during the preceding scans will not lead to the necessity of repeating the scanning, since the slices or section planes may be defined after the scanning or image data acquisition. Furthermore although three dimensional MRI may require a long time for acquiring the image data, the duration of the acquisition process is shorter than 2D according to the prior art technique. This reduces the probability of a patient displacement during the imaging session.

Any kind of volume shape can be chosen by the user. But in order to have better and immediately recognizable section plane position and orientations and instinctively recognizable relation between the image volume and the section planes a volume having the shape of a cube or of a rectangular parallelepiped can be chosen A further advantage can be also seen in the fact that the images along the different section planes being obtained by a reconstruction carried out after the three dimensional image data acquisition, the said section plane can also be partially overlaying or coinciding or can cross each other. This is not possible using the actually known methods since acquiring image data separately for each section plane the overlying or coinciding or the crossing of section planes would lead to a saturation of the nuclear spins in the regions at which the section planes or the slices are coincident or overlaps or cross each other.

This saturation would lead to black stripes on the displayed image corresponding to absence of signals.

The planes can be plane surfaces or curved surfaces. There is no theoretical limit to the shape of the plane as far as such images could have a sense for the user.

In a further embodiment of the present invention, any kind of basic MRI imaging sequence can be used such as Gradient echo, Spin echo, STIR or other actually known and used sequences. Thus it is possible to chose the basic sequence for obtaining optimum contrast.

Relating to the reconstruction of the images along the selected section planes or slices, a known technique can be used which is known with the denomination of Multi Planar Reconstruction (MPR).

The method according to the invention has also a great relevance in considering its independence from the strict maintenance of the relative position of the body under examination and the imaging volume.

Three dimensional magnetic resonance imaging and multiplanar reconstruction are known techniques. These techniques are disclosed for example in the following books: "Magnetic Resonance Imaging, Physical Principles and Sequence Design" E. Mark Haacke, Robert W. Brown, Michael R. Thompson, Ramesh Venkatesan John Wiley & Sons Inc. Publication,; "Practical NMR Imaging" M. A. Foster & J. M. S. Hutchinson IRL Press;

Acquiring three dimensional image data of the body to be examined allows always to provide for an image of the same slice of the said object without needing to provide for material references for positioning the body or part thereof to be examined always in the same position relatively to the scanning device, namely the MRI scanner.

This has been for long time a big problem in order to use the MRI as a tool for carrying out time delayed sequences of images of exactly the same slice of the body or part thereof which has to be examined. This kind of images are useful for example for follow-up examinations in order to control how a disease is evolving or how the pathology is regressing as a result of a therapy.

Due to the fact that 3D image data are acquired, the position of the body under examination or part thereof is not relevant, since the volumetric image data will always contain the zone or region of interest and will always comprise the image data which is needed to reconstruct a slice image along the identical section plane of the body under examination, provided the image volume is defined by the user in a way that it is centered or contains the zone or region of interest of the body or part thereof under examination.

According to a further embodiment, markers can be applied onto the body under examination. These markers can be used in order to identify, in an exact manner, a region of interest. Alternatively, it is possible to identify particulars of the images or of the imaged object which has a particular constancy of appearing and of position and which may be referred to in order to univocally identify regions of interest. Such particulars may consist in identifiable features of the imaged object that can be used as markers without the need of separate external markers.

The identical section plane in each volumetric image data array obtained in successive 3D-MRI sessions can be identified or reconstructed by applying a so called and well known registering technique. This technique allows using markers to define displacement vectors and thus to shift the selected section planes defined in different MRI sessions in such a way always the same section plane is chosen for reconstructing the image by shifting one section plane on the basis of the calculated shift vectors. Many registering techniques are known. Some examples are disclosed in Hemmendorf, M.; Anderson, M. T.; Kronander, T.; Knutsson, H. Phase-based multidimensional volume registration. IEE Trans Med Imaging 2002, 21, 1536-43.

According to the above, the invention relates also to a method for acquiring MRI slice images of a body or a body part along at least one selected section plane of the said body or body part, each slice image or set of slice images being acquired at different times during different and separated imaging sessions, each session providing for a new positioning of the body or a body part within an MRI scanner, the method comprising the following steps:

a) positioning the body or the body part to be imaged in the imaging zone of an MRI scanner;

b) carrying out at least one three dimensional Magnetic Resonance Imaging (3D MRI) for acquiring three dimensional anatomical data in the form of a three dimensional array of unitary volumetric image elements, so called voxels in a user defined image volume containing at least part of the anatomical district to be studied and having a predetermined orientation reference in space;

b) selecting relative to the user defined image volume at least one, preferably a set of section planes, along which the image of the anatomical region of interest or part thereof being comprised in the defined volume has to be displayed;

c) reconstructing from the said three dimensional voxel array the images along the said section plane or planes;

d) displaying and/or storing the said images as a two dimensional image;

e) storing the position and orientation parameters relative to a fixed reference or to the user defined imaging volume;

f) ending the MRI session;

g) repeating one or more times, each time after a predetermined period of time the steps a) to f) by selecting the section planes according to the stored position and orientation parameters of step e).

According to an improvement, each slice image acquired at each successive MRI session is analyzed in order to identify univocal anatomical markers the relative position of the said markers, on the slice images of each imaging session being compared and a slice shifting vector being calculated in order to modify the section plane position and orientation parameters of the successive slices if the markers' positions on the corresponding slice images do not match with the marker positions of the slice images acquired at the different MRI sessions.

Alternatively, or in combination with anatomical markers of the body or part of the body under examination, it is possible to apply external markers on the body under examination or part thereof which external markers are placed at univocally recognizable zones of the external surface shape of the said body under examination and/or of a part thereof.

The invention relates also to an apparatus for carrying out the above disclosed method.

The apparatus according to one embodiment of the invention comprises:

a) a magnetic resonance imaging apparatus comprising a Nuclear Magnetic Resonance scanner and electronic means for controlling the scanner and for processing the received data, the said means having three dimensional Magnetic Resonance Imaging (3D MRI) capabilities for acquiring three dimensional anatomical data in the form of a three dimensional array of unitary volumetric image elements, so called voxels in a defined image volume containing at least part of the anatomical district to be studied and having a predetermined orientation reference in space;

b) means for saving the three dimensional anatomical image data in a three dimensional array of image data voxels;

c) a fixed reference for defining spatial positions and orientations of the said image volume;

d) input means for univocally defining the position and or the orientation of at least one section plane or of a set of different section planes cutting the said image volume relative to the said position and orientation reference;

e) a processing unit comprising hardware and software for automatically retrieving the said volumetric image data and processing the said data in order to reconstruct from the said data the images along the said section plane or planes;

d) means for displaying the said images along the said section plane or section planes.

The methods and the apparati according to the invention and the advantages deriving therefrom will appear more clearly from the detailed description of an embodiment which is illustrated in the annexed drawings.

DETAILED DESCRIPTION OF THE PREFERRED EMBODIMENTS

Figure 1:
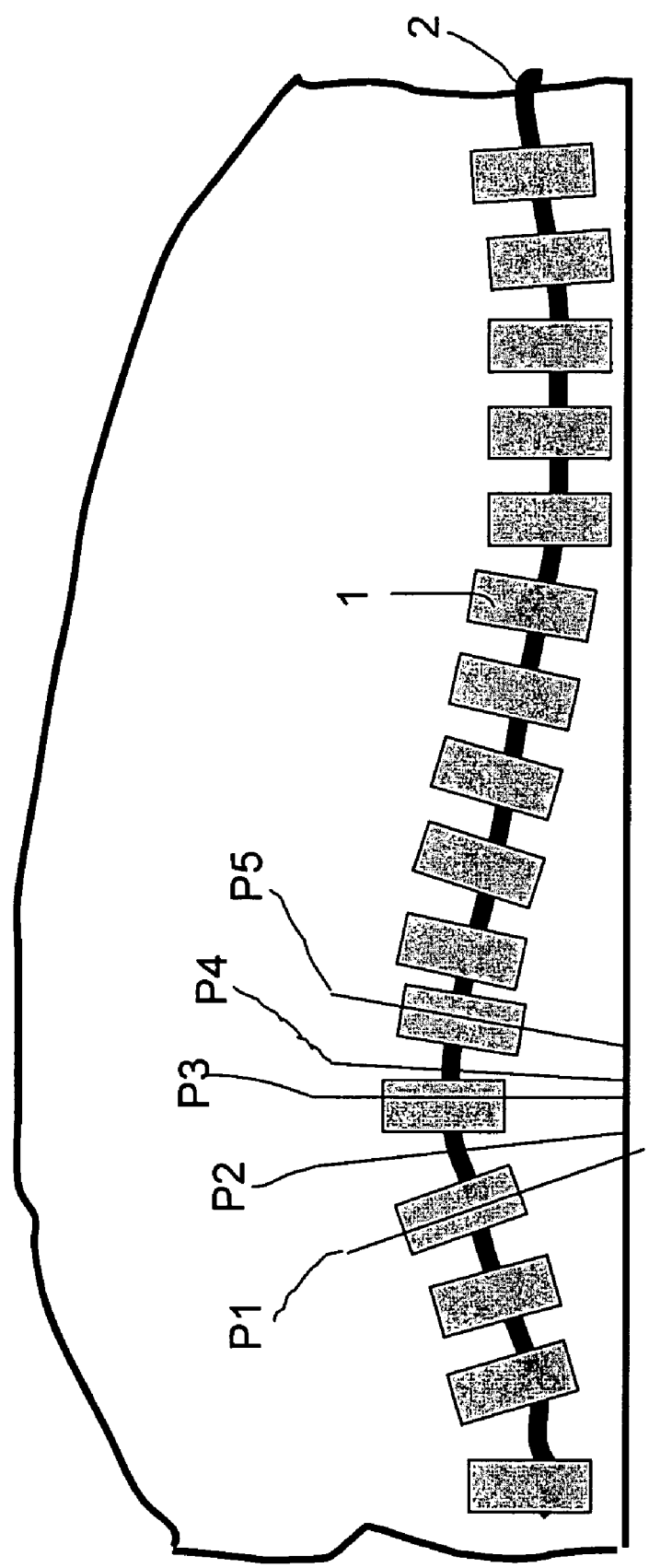
FIG. 1 illustrates the known technique by means of a lateral view of a schematic section of a human spine in which several section planes are indicated along which a slice image has to be acquired.
Figure 2:
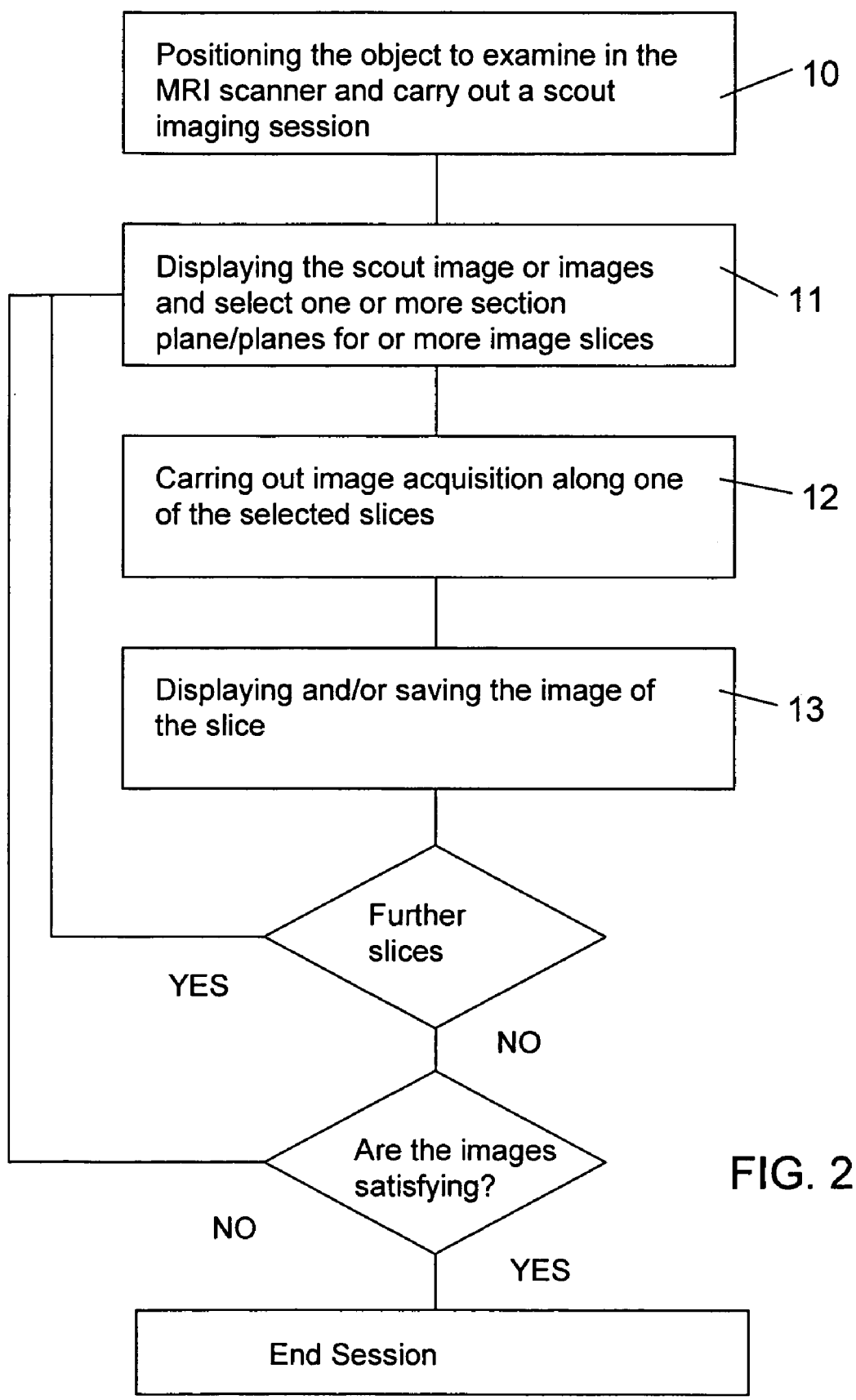
FIG. 2 is a flow diagram illustrating the main steps of the methods according to the state of the art

FIG. 1 and the flow chart of FIG. 2 show a typical scheme of a so called multislice and multiangle MRI method. A part of a human body is shown as a schematic example, where a part of the spine is visible. The grey rectangles 1 represent the vertebrae and the black line 2 indicates the axis of the spine. Five section planes are shown, indicated as P1 to P5, along which planes an image has to be acquired by applying an nuclear magnetic resonance imaging technique.

As it appears clearly the section planes, which in the real case correspond to section slices coinciding with the said planes P1 to P5 but having a finite thickness, are not parallel or at the same distance one from the other, but these section planes P1 to P5 are angled in such a way as to cut the vertebrae or the spaces between two adjacent vertebrae with a predetermined orientation which is normally chosen as the one at which the images along the planes P1 to P5 will show the maximum information or highlight some desired particulars of the anatomic structure.

According to the technique of the state of the art, for acquiring the images along the said section planes P1 to P5 or the corresponding slices, the following steps are applied. As a first step indicated by 10 in FIG. 2, the object to be examined is positioned in the MRI scanner and centered with the imaging volume provided within the scanner. Typically, the imaging volume is a part of a body housing or positioning cavity defined by the scanner structure, in which part optimum magnetic field conditions of the static magnetic field are ensured in order to allow acquisition of high quality images.

As a next step, a first image acquisition is carried out in order to acquire an image of the body, or of the part of it to be examined, along some predetermined section planes. These section planes are typically oriented in such a way that the so-called scout or guide images give a panoramic view of the body under examination which can help define the section planes (P1 and P5 according to the example of FIG. 1) along which it is desired to acquire images of the body under examination or of a part thereof. FIG. 1 is a good example of a scout or guide image which has been taken along a front-rear section plane oriented in the longitudinal direction of the spine and cutting the spine approximately at the center thereof. More than one guide image can be acquired.

As the step indicated by 11 in FIG. 2, the acquired scout or guide images are displayed and the operator can chose one or more section planes giving the parameters of their orientations relative to the scout image or scout images and relative to each other. As appears clearly from FIG. 1, the slices or section planes P1 to P5 have different orientations relative only to one axis of rotation or angular displacement, which in the example of FIG. 1 is an axis directed perpendicularly to the drawing sheet.

As a further step indicated by 12 in FIG. 2, the imaging session is carried out to acquire one after the other the image data along each of the selected section planes. Referring to the example of FIG. 1, this means that the images are acquired along each one of the section planes therein selected and indicated by P1 to P5.

At step 13, the acquired image data is displayed either by displaying one after the other in a temporal sequence each image along each of the said section planes selected, or by displaying the said images one beside the other on the monitor screen.

At this step the imaging sequence could be ended. Nevertheless if images along further slices are needed or if the images along the selected slices are not satisfying per se or relative to the section planes chosen, the whole process has to be repeated returning to step 11 and thus repeating the displaying of the scout or guide images and the selection of the section planes by choosing their parameter of orientation relative to the scout or guide images and to each other, carrying out again steps 12 and 13.

Particularly, step 12 is a critical one since the patient may not have maintained the original position at which the scout image or images has been acquired, so that the section plane selection of step 11 could not correspond anymore to the real position of the patient. In this condition, the entire process could be repeated by returning to step 10. In any case this would lead to a considerable loss of time. It has to be noticed that such a solution could be objectively chosen by the operator if he would become aware of a displacement of the patient having been carried out after having acquired the scout images. In this case the solution of repeating the entire process form the beginning, namely form step 10 could be logical. On the other hand, if the operator has not become aware of any displacement of the patient, the solution of repeating the entire process from the beginning, i.e., from step 10, would be based only on a hypothesis which could or could be not real. So, no clear and univocal evidence could be ensured to the operator about the reason for a certain loss of quality of the images or for a displacement of the section planes chosen from the real one at which the imaging has been carried out.

Figure 3:
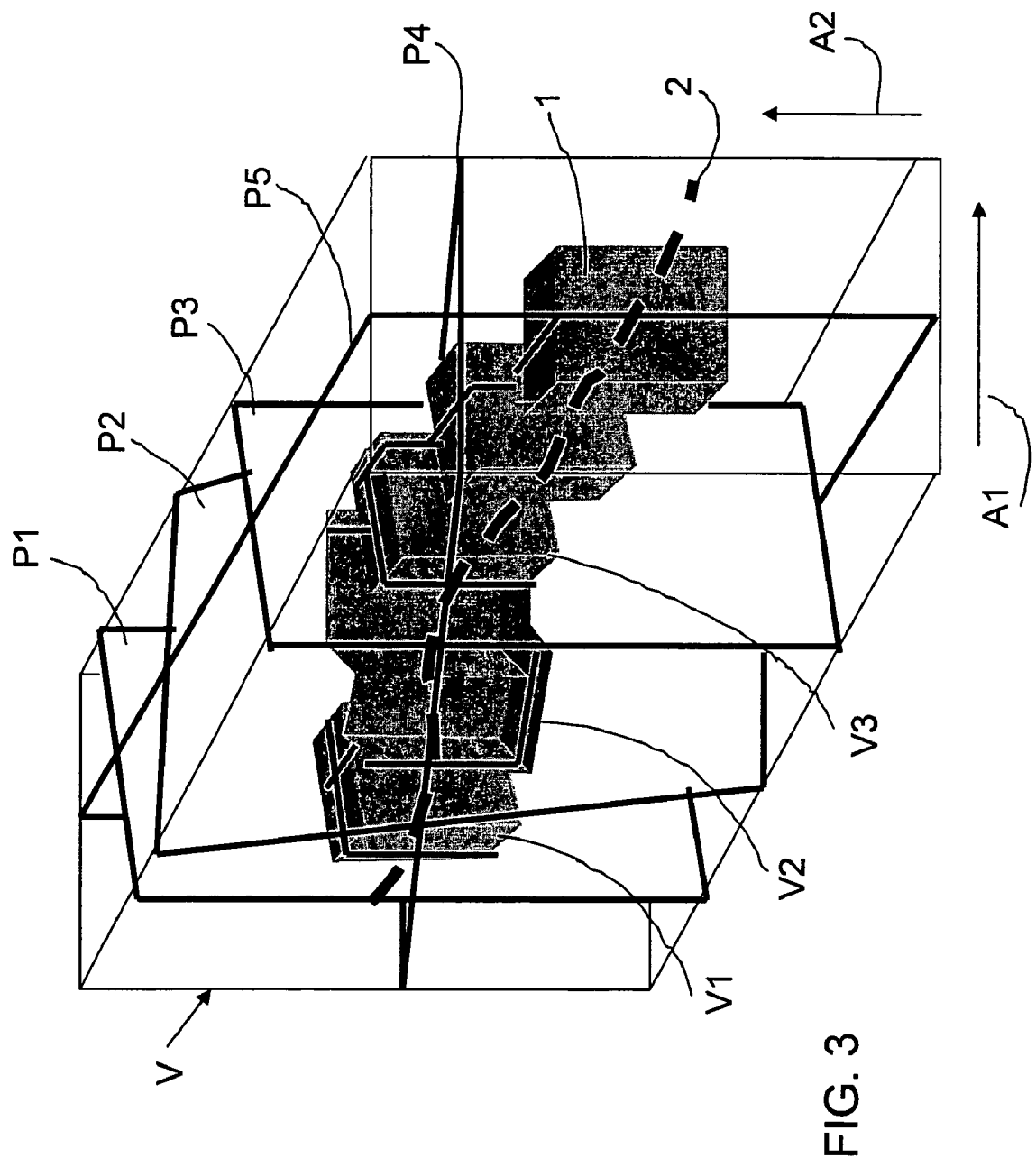
FIG. 3 is a schematic perspective view of a spine section of a user defined image volume being indicated and selected section planes along which a MRI slice image has to be reconstructed.

FIG. 3 shows schematically a volume V containing a part of a spine, where the gray parallelepipeds represent the individual vertebrae 1, the discontinuous line represents the axis of the spine 2, and where three section planes P1, P2, P3 are illustrated which have different orientations in space relative to one another and to the volume enclosing surface and which cut the vertebrae indicated with V1, V2, V3. A fourth section plane P4 is oriented transversally relative to the other three section planes P1, P2, P3 and is slightly angled relative to the horizontal plane, presuming that the volume V is oriented with its base lying in a horizontal plane. Section plane P5 is the section plane along which a guide image is taken, which is similar to the one illustrated in FIG. 1.

This schematic representation tries to visualize in a simplified form the conditions according to an embodiment of the method of the present invention. The steps of the method being summarized in the diagram of FIG. 4.

As might be appreciated, FIG. 3 clearly illustrates that the section planes or image slices P1, P2 and P3 are angled one with respect to the other, not only according to one axis of rotation or of angular displacement which is parallel to the arrow A1 but also according to an axis of rotation or of angular displacement that is perpendicular to the first one and which is parallel to the arrow A2 in FIG. 3.

Step 20 differs from step 10 of the prior art method in the fact that instead of carrying out a first imaging session in order to acquire images along one or more section planes corresponding to guide images along selected slices of the body under examination or of part thereof, which in the case of example of FIG. 1 is a part of the spine, a three dimensional image acquisition procedure is carried out, within a volume which the operator has defined in such a way as to contain the region of the body to be examined.

Thus at the first step 20 the entire image information in the form of volumetric image data, as for example a three dimensional array of unitary three dimensional image points, so-called voxels, is acquired. At step 21 the volumetric image data is stored in an image data memory.

At step 22 one or more section planes are selected along which guide images have to be reconstructed. In the example of FIG. 3, the section planes for the guide images could be for example the section plane P5, which would lead to an image similar to the one of FIG. 1, and the section plane P4, which would lead to a further guide image along a transversal plane.

The said images are reconstructed by simply retrieving the volumetric imaged data and determining by means of the position and orientation parameters of the said section planes P4 and P5, relative to the volume V, which voxels fall within the said planes. Thus, two dimensional arrays of image data are formed which can be displayed. Such technique is well known in the art and is called Multi Planar Reconstruction.

At step 22 one or more section planes are selected along which guide images have to be reconstructed. In the example of FIG. 3, the section planes for the guide images could be for example the section plane P5, which would lead to an image similar to the one of FIG. 1, and the section plane P4, which would lead to a further guide image along a transversal plane. In one embodiment, the section plane or section planes along which the guide image or images is automatically reconstructed and displayed are factory default settings.

The said images are reconstructed by simply retrieving the volumetric imaged data and determining by means of the position and orientation parameters of the said section planes P4 and P5, relative to the volume V, which voxels fall within the said planes. Accordingly, each anatomical district can be associated to one or more different section planes for one or more guide image or images forming a table of association of the different section planes with the different anatomical districts. Thus, two dimensional arrays of image data are formed which can be displayed. Such technique is well known in the art and is called Multi Planar Reconstruction.

Figure 4:
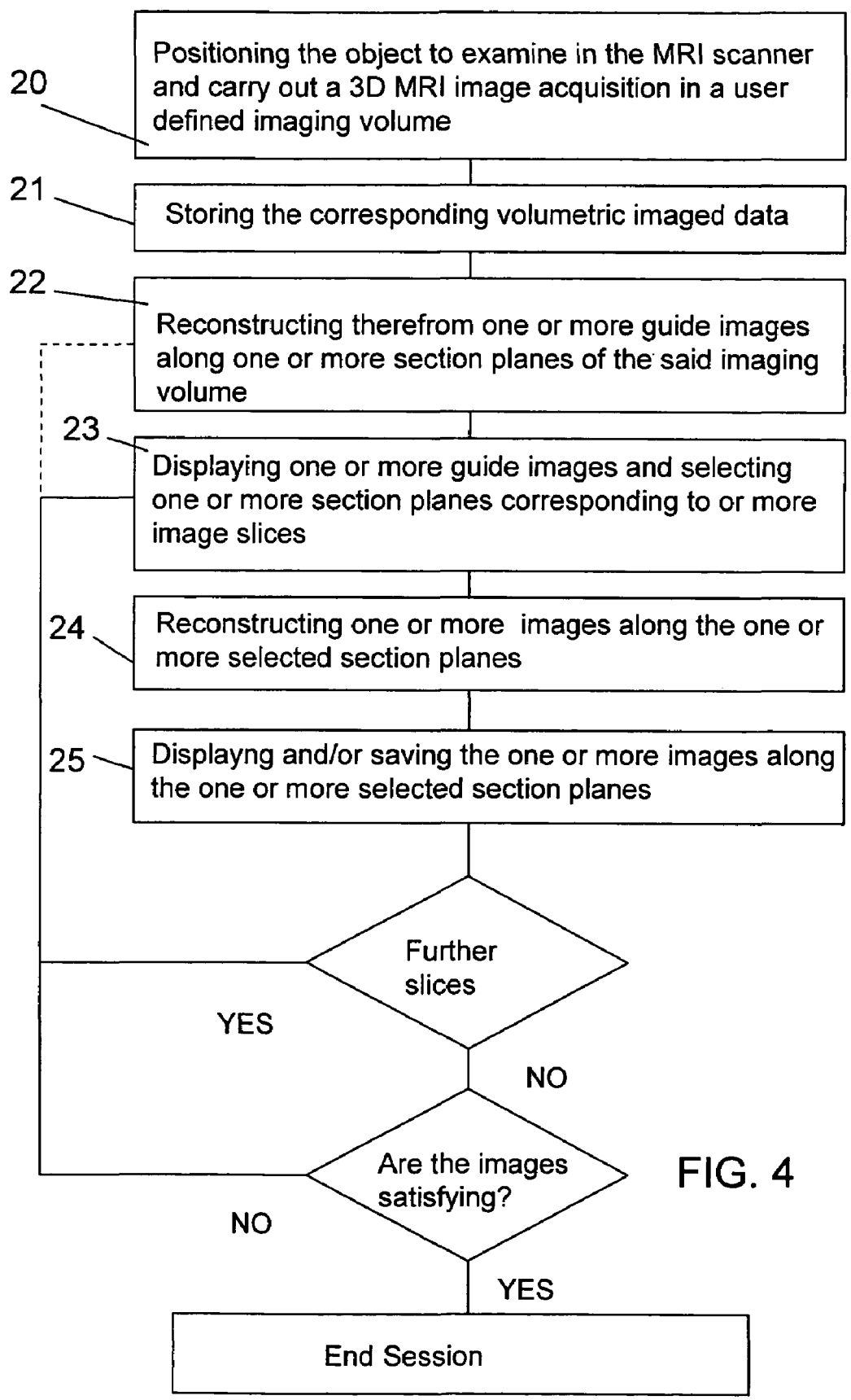
FIG. 4 is a flow diagram illustrating the main steps according to an embodiment of the present invention.

As it appears clearly from FIG. 4, if images along further section planes are needed or if the section planes selected give unsatisfying images so that at least some of the section planes have to be newly selected with other positions or orientations as the previously defined ones, according to the method of the present invention, it is not necessary to repeat the entire process from the beginning, namely from step 20. This means that no image data acquisition procedure has to be carried out again, but the already stored volumetric image data can be retrieved from the memory and the steps 22 to 25 can be repeated.

This means that the scanning of the patient needs to be carried out only one or more times but at only one step during a limited but continuous period.

It has to be noted that in the example of FIG. 3, a rectangular shaped volume V has been chosen for sake of simplicity but this fact has not to be considered as a limitation of the method according to the present invention, since no limit is put to the shape of the volume that can be chosen by the operator. Also, no limitation has to be put to the shape of the surfaces forming the section planes which can also show a curved surface along only one, two or three dimensions, the planes being illustrated as having plane surfaces only for sake of simplicity.

Acquiring three dimensional images gives also further advantages that can be better understood by means of FIGS. 5A to 5D.

FIGS. 5A to 5D show schematic views of different MRI sessions carried out at different times, each time positioning the hand in the scanner and each time defining an imaging volume enclosing the hand, markers being provided at selected identical positions on the hand for carrying out a slice image registration in order to identify at each imaging session the same section plane across the hand along which a slice image has to acquired and displayed.

Follow up examinations is a very important tool for analyzing the developments of a disease or the response to a therapy. Generally today, MRI is considered not to be useful for follow up examinations due to the fact that it is not simple to position the body under examination exactly in the same position at each imaging session. This problem can be overcome by using the method according to the invention. By acquiring volumetric image data of the body under examination, the entire information is always provided in the three dimensional data set, providing the defined scanned volume encloses the entire body to be examined or the entire part of it to be examined.

Thus the problem lies only to determine the same section plane across the imaged part at any session by considering that the plane could not have and probably will not have the same orientation in space relative to the volume defined by the user in a session as the section planes or plane defined in a preceding session.

FIGS. 5A to 5D try to show this situation by representing a hand as a body part to be examined by MRI, and the volume V defined by the user and in which the image data has to be acquired. Considering for simplicity that this volume is always the same at each imaging session, the hand can be differently positioned at each session relative to the volume with respect to all the other sessions. Thus, section plane P1A defined in the session represented by FIG. 5A will correspond if referred to the hand as a body part under examination to section plane P1B, P1C and P1D in the following imaging sessions represented by FIGS. 5B to 5D.

In order to identify the correct section plane one, preferably at least two or more, markers can be provided. The markers can be, as illustrated in FIG. 5A to 5D, NMR opaque elements 30 which can be positioned on the body under examination at univocally and repeatedly identifiable points of the anatomy or shape of the said body.

Alternatively, the markers can be parts or zones of the anatomy of the body under examination which are univocally recognizable as particularly evident zones and which are constant. This allows the use of these zones as intrinsic markers.

Combinations of these anatomic markers and of the opaque elements can also be used.

These markers can be searched and identified within each of the volumetric image data acquired at each imaging session. The markers can be used to align spatially the volumetric image data by applying a so called Registering algorithm. These algorithms are known in the art and the image registration technique using these algorithms is described for example in Hemmendorf, M.; Anderson, M. T.; Kronander, T.; Knutsson, H. Phase-based multidimensional volume registration. IEE Trans Med Imaging 2002, 21, 1536-43.

Figure 5A:
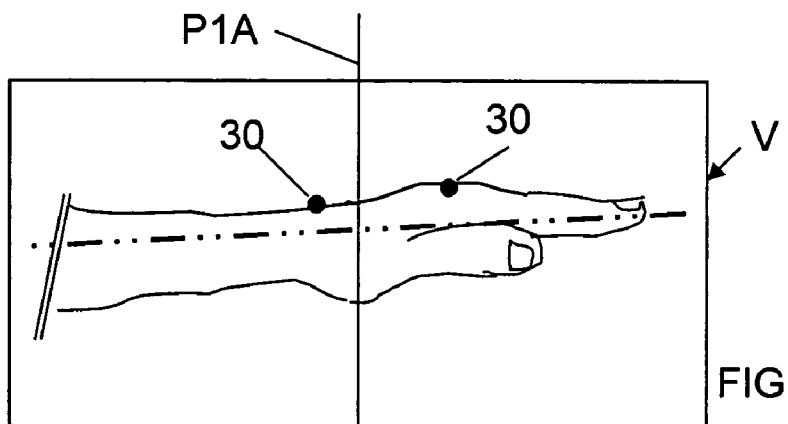
FIGS. 5A to 5D shows schematic views of different MRI sessions carried out at different times, each time positioning the hand in the scanner and each time defining an imaging volume enclosing the hand, markers being provided at selected identical positions on the hand for carrying out a slice image registration in order to identify at each imaging session the same section plane across the hand along which a slice image has to acquired and displayed.
Figure 5B:
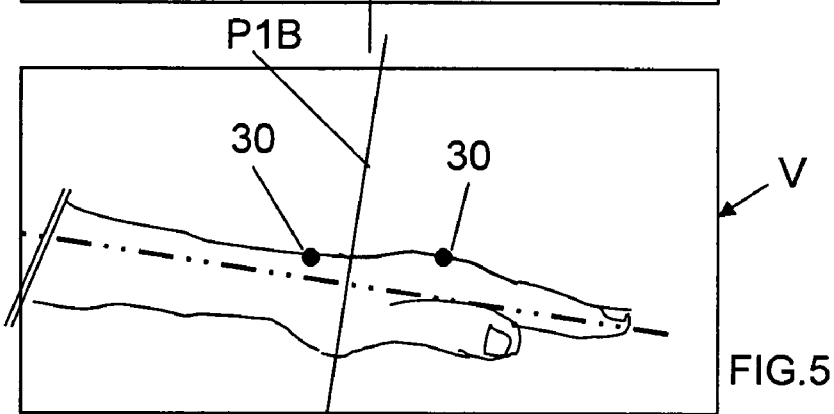
Figure 5C:
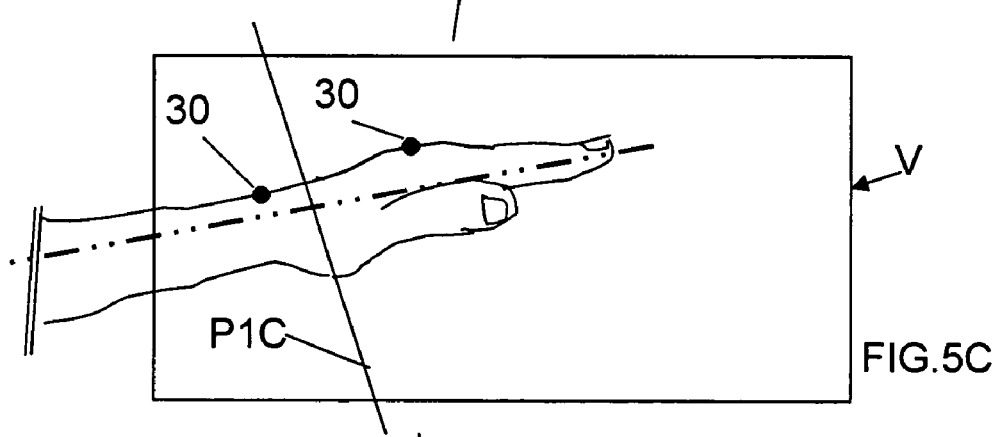
Figure 5D:
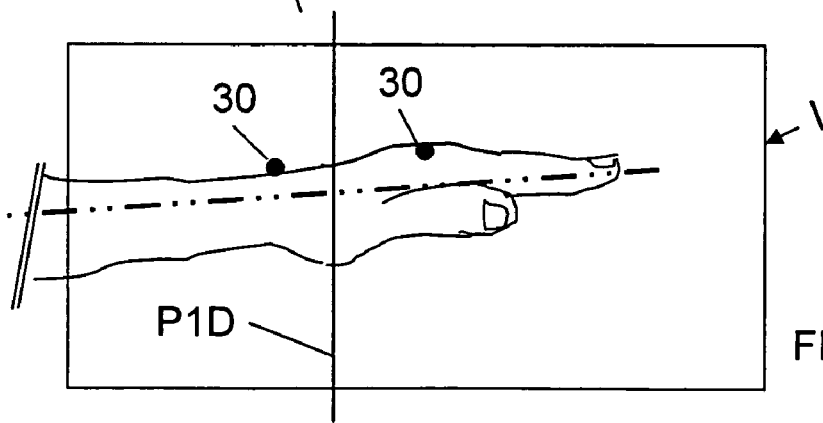

Thus, using these techniques, the plane P1A can be correctly repositioned relative to the imaged object (namely the hand) in the image data of the following imaging sessions giving to it the correct orientation as indicated by P1B, P1C, P1D in FIGS. 5B, 5C, 5D.

The position of the object to be imaged, namely the hand can be identified and displacement vectors can be determined with reference to the position of the hand in FIG. 5A, which displacement vectors can be used by calculating the new position and orientation parameters of the plane P1A relative to the different positions of the hand in each of the following imaging sessions.

Thus, for each imaging session, the same section plane can be identified and an image can be reconstructed along this section plane allowing comparisons to be carried out between them in order to identify the developments for example of a disease or of a therapy which has occurred from one first imaging session to the successive ones or ones.

Figure 6:
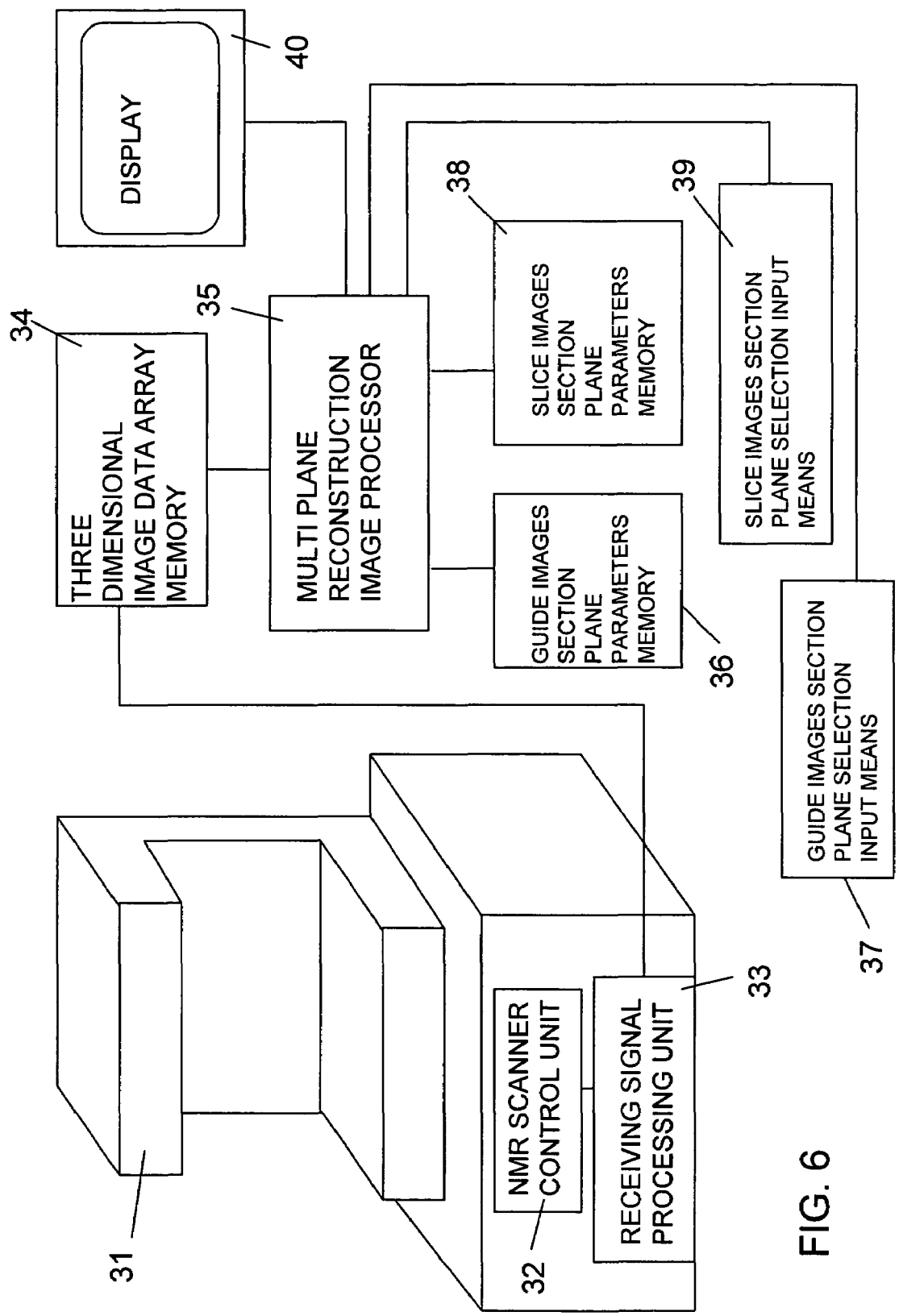
FIG. 6 is a schematic block diagram showing an embodiment of an apparatus according to the present invention.

FIG. 6 shows a block diagram of an apparatus for carrying out nuclear magnetic resonance imaging according an embodiment of to the method of the present invention.

A scanner 31 comprising a magnetic structure defining a cavity for positioning a body to be examined or a part thereof is provided with means for generating a static magnetic field, means for generating NMR excitation pulses and for receiving NMR signals. The scanner 31 and the above mentioned means are controlled by a NMR scanner control unit 32. The NMR signals emitted by the body under examination or a part thereof are received by a receiving antenna (not shown) and processed into volumetric image data by a receiving signal processing unit 33. The volumetric image data acquired by applying three dimensional MRI techniques well known at the state of the art are stored in a memory 34. A multiplane reconstruction image processor 35, comprising processor hardware which carries out a multiplane reconstruction program, is connected to a memory or a memory area 36 where the parameters relative to the position and orientation of the section plane or planes for the guide images are stored. These parameters can be defined by the producer of the apparatus or can be inputted by the user by means of guide images section plane selection input means 37. Similarly, in a memory or in a memory area 38 the parameters for the slice images section planes are stored. These parameters are defined by the user and inputted to the memory by means of input means 39. Display means 40 are connected to the multiplane reconstruction image processor 35 for displaying the guide images and the slice images selected.

The input means can be of any kind. For example, parameters relative to the position and orientation of the section planes either for the guide images and for the slice images can be inputted in the form of numeric and/or alphanumeric data by means of a keyboard.

Alternatively, or in combination, graphic input means can be provided. In this case, the selection of the section plane or planes for the slice images can be carried out by tracing the planes as lines on the guide image or guide images. The lines traced are converted in numeric data from which the position and orientation of the section plane or planes can be calculated. The guide images can consist in one or more two dimensional images taken along predefined section planes or a three dimensional image can be displayed on the monitor simulating also the dimension perpendicular to the image plane by a assonometric projection or using a perspective view which assonometric projection or which perspective views are reconstructed from the volumetric imaged data and the planes can be traced in these three dimensional image.

According to a further embodiment of the method of the present invention, also an image registration processor can be provided which can be formed by the same hardware of the multi plane reconstruction processor in which a registration program is carried out consisting in a registration algorithm.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An apparatus for carrying out an image acquisition and display by means of Nuclear Magnetic Resonance Imaging, which apparatus comprises:
   a) a magnetic resonance imaging apparatus comprising a Nuclear Magnetic Resonance scanner and an electronic controller controlling the scanner and for processing data received from the scanner, the controller having three dimensional Magnetic Resonance Imaging capabilities for acquiring three dimensional anatomical image data in the form of a three dimensional voxel array of unitary volumetric image elements in a defined image volume containing at least part of an anatomical district to be studied and having a predetermined orientation reference in space;
   b) a memory for saving the three dimensional anatomical image data in the three dimensional voxel array;
   c) a fixed reference for defining spatial positions and orientations of the image volume;
   d) an input for defining a position or an orientation of at least one section plane or of a set of different section planes cutting the image volume relative to the position or orientation;
   e) a processing unit comprising hardware and software for retrieving the anatomical image data and processing the anatomical image data in order to reconstruct from the anatomical image data images along the section plane or planes;
   f) a display for displaying the images along the section plane or section planes;
   g) a memory for storing a list of possible different section planes along which a guide image or guide images can be reconstructed;
   h) a memory in which a list of different anatomical districts is saved, which anatomical districts relate to typical MRI examinations to be carried out by the magnetic resonance imaging apparatus;
   i) means for associating each anatomical district to one or more different section planes for one or more guide image or guide images to form a table of association of the different section planes with the different anatomical districts; and
   k) selection means manually activatable for manually selecting a kind of anatomical district to be imaged and means for loading into the processing unit a corresponding parameter of the section plane or planes along which the corresponding guide image or guide images to be automatically displayed for the section plane or section planes selection along which the guide image or guide images has to be reconstructed form the 3D volumetric image data;
   wherein the input is formed by visual input means, the input comprising:
   means for automatically displaying the one or more guide images along one or more predetermined section planes;
   predefined section plane or section planes parameters automatically retrieved by the processing unit;
   means for selecting the position or the orientation of a desired section plane or planes by drawing, dragging or orienting lines representing the section planes along the said guide image or images; and
   means for automatically reading the position and orientation parameters of the desired selected section plane or planes from the position of the line or lines drawn onto the guide image or images and feeding the said parameters to the processing unit.

2. The apparatus according to claim 1, wherein the processing unit comprising hardware and software for automatically retrieving the anatomical image data and processing the anatomical image data in order to reconstruct from the anatomical image data the images along the said section plane or planes is a Multi Planar Reconstruction Unit.

3. The apparatus according to claim 2, further comprising means for repeatedly activating the input device, the processing unit and the display without activating the MRI scanner and electronic controller.

4. The apparatus according to claim 1, wherein the section plane or section planes along which the guide image or images is automatically reconstructed and displayed are factory default settings.

5. The apparatus according to claim 1, wherein the section plane or section planes along which the guide image or images has to be automatically reconstructed and displayed are defined by the user.

* * * * *